US00PP23646P2

(12) United States Plant Patent
Eggleton

(10) Patent No.: US PP23,646 P2
(45) Date of Patent: May 28, 2013

(54) ***GAURA* PLANT NAMED 'PASSIONATE RAINBOW PETITE'**

(50) Latin Name: *Gaura lindheimeri*
Varietal Denomination: PASSIONATE RAINBOW PETITE

(76) Inventor: Steve Eggleton, Wonga Park (AU)

( * ) Notice: Subject to any disclaimer, the term of this patent is extended or adjusted under 35 U.S.C. 154(b) by 0 days.

(21) Appl. No.: 13/373,867

(22) Filed: Dec. 1, 2011

Related U.S. Application Data

(60) Provisional application No. 61/459,514, filed on Dec. 15, 2010.

(51) Int. Cl.
*A01H 5/00* (2006.01)

(52) U.S. Cl.
USPC ..... Plt./432

(58) Field of Classification Search ..... Plt./432
See application file for complete search history.

*Primary Examiner* — Annette Para

(57) ABSTRACT

A new cultivar of *Gaura* plant named 'PASSIONATE RAINBOW PETITE' that is characterized by dense compact and mounding habit, short height, bright red stems, dark-pink buds opening to medium-pink flowers and new flush of foliage growth that is bright pink-red in color. In combination these traits set 'PASSIONATE RAINBOW PETITE' apart from all other existing varieties of *Gaura* known to the inventor.

3 Drawing Sheets

Genus: *Gaura.*
Species: *lindheimeri.*
Denomination: 'PASSIONATE RAINBOW PETITE'.

BACKGROUND OF THE INVENTION

The present invention relates to a new and distinct variety of butterfly bush grown as an ornamental plant for use in containers and in the landscape. The new cultivar, in the family Onagraceae is known botanically as *Gaura lindheimeri* and will be referred to hereinafter by the cultivar name 'PASSIONATE RAINBOW PETITE'.

'PASSIONATE RAINBOW PETITE' was discovered by the inventor as a naturally occurring sport, of the parent an individual *Gaura* 'Passionate Rainbow' (U.S. Plant Pat. No. 17,002). 'PASSIONATE RAINBOW PETITE' was discovered in June 2007 growing in the inventor's commercial crop of 'Passionate Rainbow' at the inventor's nursery in Victoria, Australia. The inventor selected 'PASSIONATE RAINBOW PETITE' based on the criteria of short internodes and high plant density, which distinguish 'PASSIONATE RAINBOW PETITE' from the parent.

The distinguishing characteristics of 'PASSIONATE RAINBOW PETITE' are compact habit, short height, higher branching without pruning, and profuse quantity of flowers. The closest comparison plants are *Gaura* 'Passionate Rainbow' and *Gaura* 'Bijou Butterflies' (U.S. Plant Pat. No. 15,479). 'PASSIONATE RAINBOW PETITE' is distinguishable from 'Passionate Rainbow' in height and habit, branching, and flower quantity. 'PASSIONATE RAINBOW PETITE' is distinguishable from 'Bijou Butterflies' by stronger plant vigor, shorter height, and narrow leaves.

'PASSIONATE RAINBOW PETITE' exhibits dense compact, and mounding habit, dark pink buds opening to medium-pink flowers, and bright red stems. New flush of foliage growth is bright pink-red in color, while mature foliage is mid-green in color with fine cream margins. Plant dimensions the first year and at maturity are 40 cm in height and 40 cm in width. Bloom period is from early summer into fall. Cultural requirements are moist well-draining soil, and full sun, with moderate to infrequent water. 'PASSIONATE RAINBOW PETITE' is hardy in USDA Zones 7 and higher.

The first asexual propagation of 'PASSIONATE RAINBOW PETITE' was conducted in 2007. Asexual propagation was carried out by the inventor at the inventor's nursery in Victoria, Australia using the method of softwood cuttings. The inventor has determined that 'PASSIONATE RAINBOW PETITE' is stable and reproduces true to type during successive generations of asexual reproduction.

SUMMARY OF THE INVENTION

The following traits have been repeatedly observed and represent the distinguishing characteristics of the new *Gaura* cultivar 'PASSIONATE RAINBOW PETITE'. In combination these traits set 'PASSIONATE RAINBOW PETITE' apart from all other *Gaura* known to the inventor. 'PASSIONATE RAINBOW PETITE' has not been tested under all possible conditions and phenotypic differences may be observed with variations in environmental, climatic and cultural conditions, however, without any variance in genotype.

1. 'PASSIONATE RAINBOW PETITE' exhibits dense compact, and mounding habit.
2. The buds of 'PASSIONATE RAINBOW PETITE' are dark-pink in color, opening to flowers that are medium-pink in color.
3. 'PASSIONATE RAINBOW PETITE' blooms continually from early summer into fall.
4. The new flush of foliage growth on 'PASSIONATE RAINBOW PETITE' is bright pink-red in color.
5. The mature foliage of 'PASSIONATE RAINBOW PETITE' is mid green in color with fine margins that are cream-white in color.
6. The stems of 'PASSIONATE RAINBOW PETITE' are bright red in color.
7. 'PASSIONATE RAINBOW PETITE' is hardy in USDA Zones 7 and higher.

8. 'PASSIONATE RAINBOW PETITE' is 40 cm. in height and 40 cm. in width as a mature plant after one year of growth.

BRIEF DESCRIPTION OF THE DRAWINGS

The accompanying color drawings illustrate the overall appearance of the new *Gaura* cultivar named 'PASSIONATE RAINBOW PETITE' showing color as true as is reasonably possible to obtain in color reproductions of this type. Color in the drawings may differ from color values cited in the detailed botanical description, which accurately describe the actual color of 'PASSIONATE RAINBOW PETITE'.

The drawing labeled

The drawing labeled

The drawing labeled

Figure 1:
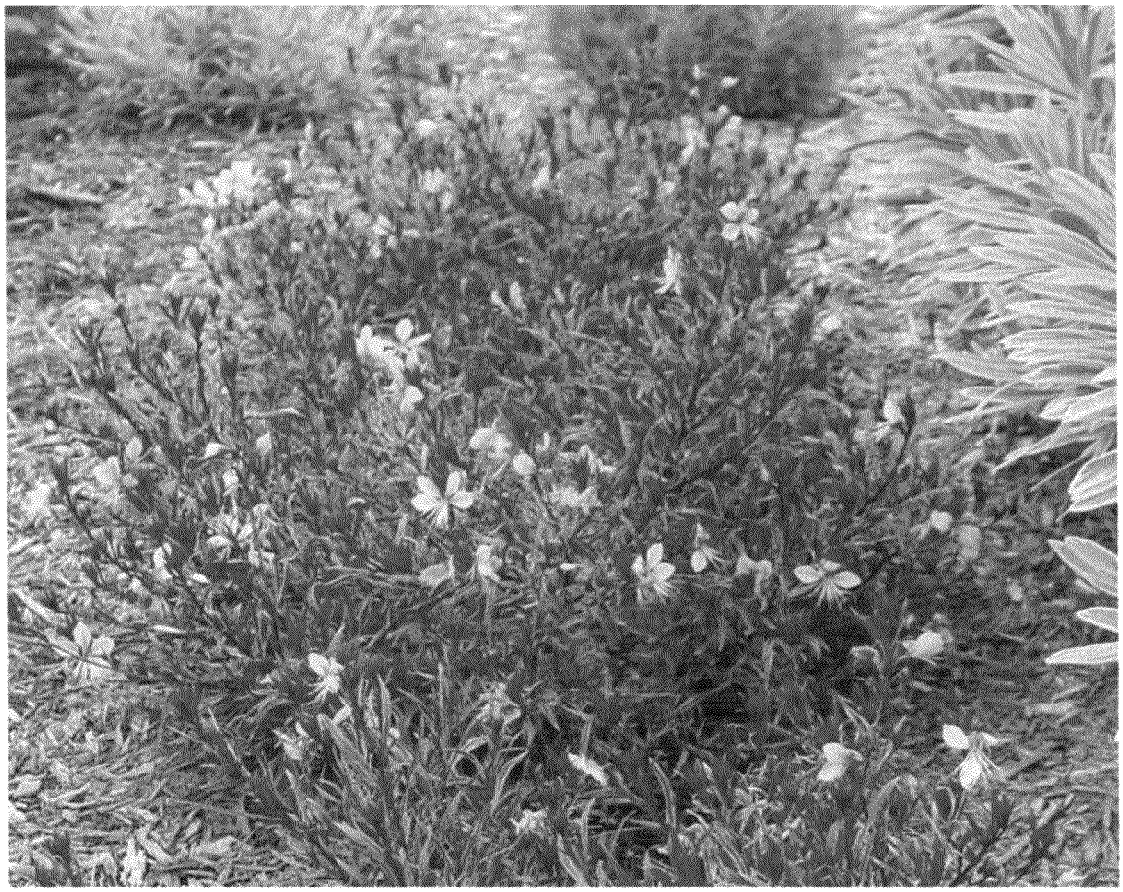
FIG. 1 depicts a whole plant of 'PASSIONATE RAINBOW PETITE' illustrating the habit. The plant is nine months old and has been grown out of doors in Lancaster, Pa.
Figure 2:
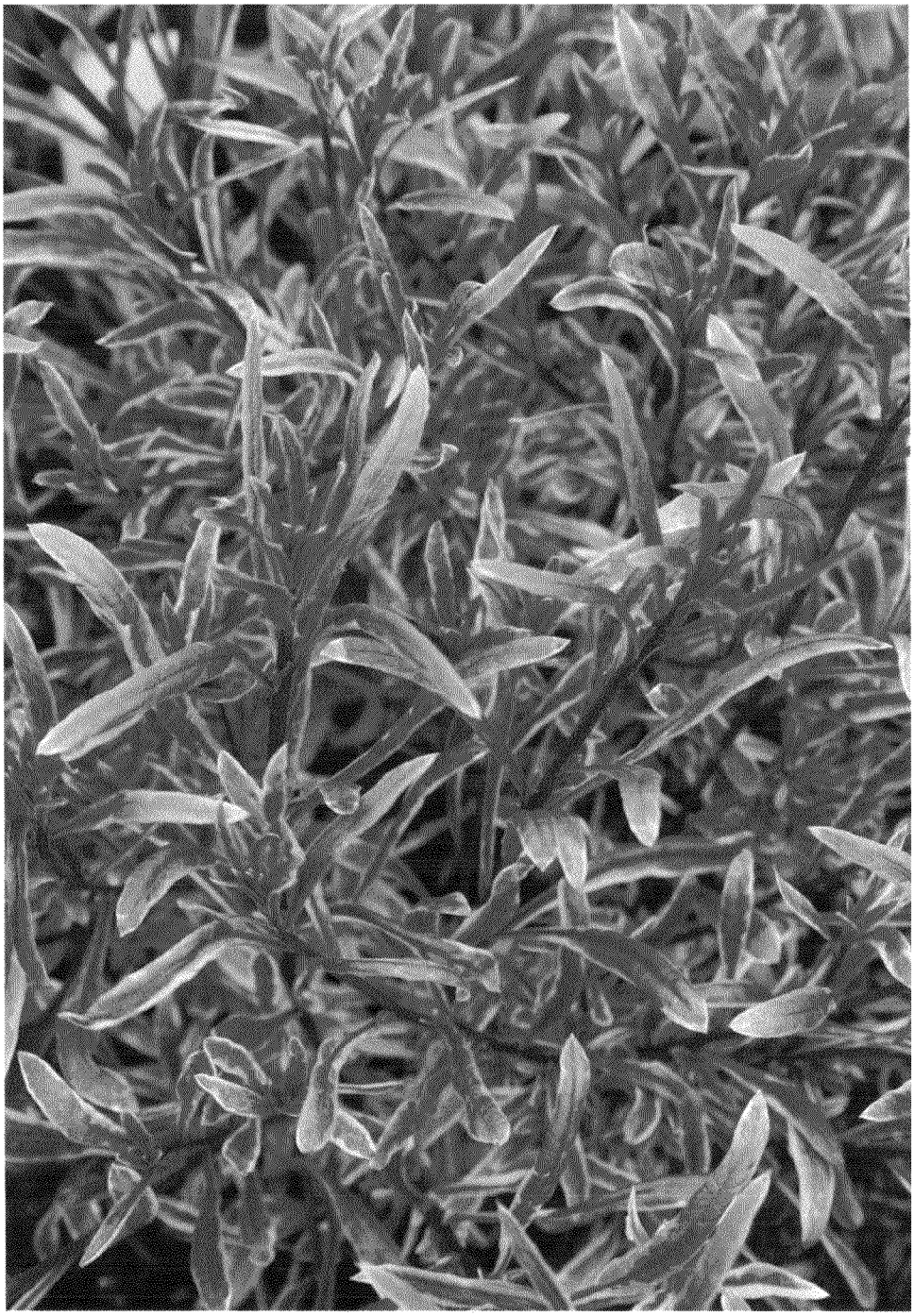
FIG. 2 depicts a close-up view of the newly flushed foliage growth on plants grown by the inventor in Melbourne, Victoria, Australia.
Figure 3:
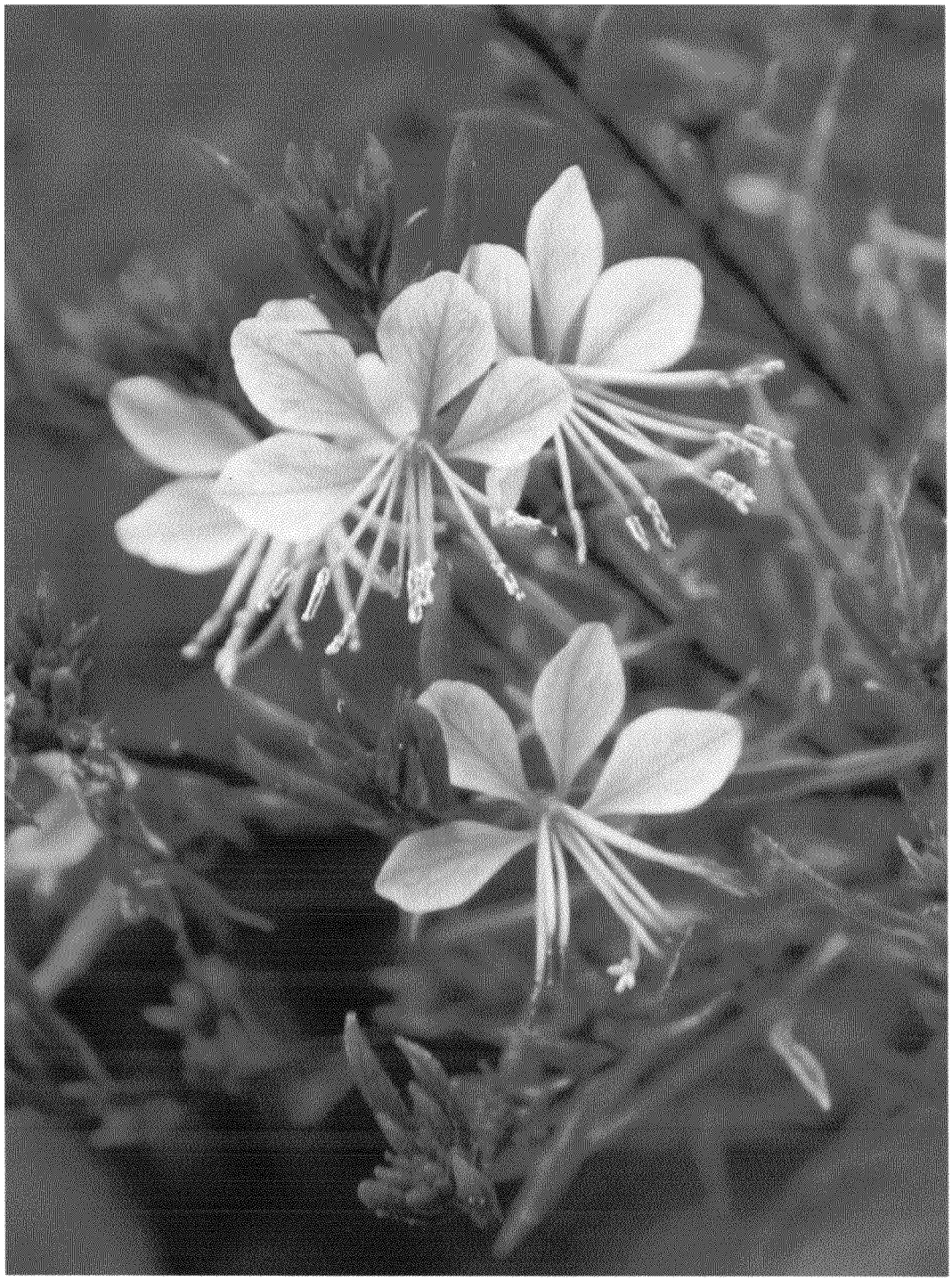
FIG. 3 is a close-up view of the flowers and buds on plants grown by the inventor in Melbourne, Victoria, Australia.

Color in the drawings may appear different from actual color due to light reflectance, but are as close as is reasonably possible to obtain by conventional photography.

BOTANICAL DESCRIPTION OF THE PLANT

The following is a detailed botanical description of the new *Gaura* variety named 'PASSIONATE RAINBOW PETITE'. Data was collected in Arroyo Grande, Calif. from a 12-month-old plant grown in a 1-litre container out-of-doors in full sun. The color determinations are in accordance with The 2001 Royal Horticultural Society Colour Chart of London, England, except where general color terms of ordinary dictionary significance are used. The growing requirements are similar to other *Gaura*.

Botanical classification: *Gaura lindheimeri* 'PASSIONATE RAINBOW PETITE'.
Family: Onagraceae.
Genus: *Gaura*.
Species: *lindheimeri*.
Denomination: 'PASSIONATE RAINBOW PETITE'.
Common name: Butterfly bush.
Commercial classification: Perennial.
Use: Ornamental plant for use in containers and in the landscape.
Cultural requirements: Plant in moist well-draining soil, and full sun, with moderate to infrequent water.
Vigor: Strong.
Pests and disease: Susceptible to mites.
Parentage: *Gaura lindheimeri* 'PASSIONATE RAINBOW PETITE' was discovered as a naturally occurring sport of the parent, an individual *Gaura lindheimeri* 'Passionate Rainbow' (U.S. Plant Pat. No. 17,002).
Plant description:
- *Container plant size.*—1-litre.
- *Bloom period.*—Early summer into fall.
- *Habit.*—Dense compact and mounding.
- *Dimensions* (*first year*).—40 cm in height and 40 cm in width.
- *Dimensions* (*at maturity*).—40 cm in height and 40 cm in width.
- *Hardiness.*—USDA Zones 7 and higher.
- *Propagation.*—Propagation is accomplished using the method of softwood cuttings.
- *Time to develop roots.*—2-3 weeks from initial cutting.
- *Crop time.*—6-9 months to produce a plant in bud and flower in a 1-litre container.

Stem:
- *Branching* (*range*).—Basal to cauline.
- *Shape.*—Cylindrical.
- *Main stem surface.*—Scurfy.
- *Main stem color.*—N199B.
- *Main stem diameter* (*average*).—1.50 cm.
- *Lateral branch quantity* (*average*).—14 per 1-litre container plant.
- *Lateral branch color.*—59A.
- *Lateral branch length* (*average*).—10 cm.
- *Lateral branch diameter* (*range*).—3 mm to 5 mm.
- *Stem surface* (*range*).—Puberulent to glabrous.
- *Internode* (*range*).—5 mm to 2 cm.

Foliage:
- *Leaf quantity* (*range*).—64-128 per lateral branch.
- *Shape.*—Oblanceolate.
- *Division.*—Simple.
- *Apex.*—Acute.
- *Base.*—Attenuate.
- *Margin.*—Entire.
- *Venation pattern.*—Pinnate with prominent mid-vein.
- *Abaxial and adaxial vein color* (*mature foliage*).—61A.
- *Abaxial and adaxial vein color* (*new growth foliage*).—61A.
- *Margins.*—Entire.
- *Attachment.*—Sessile.
- *Arrangement.*—Whorled.
- *Abaxial leaf surface* (*range*).—Puberulent to glabrous.
- *Adaxial leaf surface* (*range*).—Puberulent to glabrous.
- *Leaf appearance* (*abaxial and adaxial surface*).—Matte.
- *Leaf length* (*range*).—1.5 cm to 5.50 cm.
- *Leaf width* (*range*).—0.20 cm to 0.75 cm.
- *Mature leaf color* (*abaxial surface*).—138B and 159A.
- *Mature leaf color* (*adaxial surface*).—138B and 159A.
- *New flush leaf color abaxial surface* (*range*).—61A to 61D.
- *New flush leaf color adaxial surface* (*range*).—61A to 61D.
- *Fragrance.*—None observed.

Flowers:
- *Inflorescence.*—Raceme.
- *Flower quantity per inflorescence* (*range*).—10-15.
- *Bud quantity per inflorescence* (*range*).—10-15.
- *Lastingness of flower.*—24 hours.
- *Flower depth.*—2.75 cm.
- *Flower diameter.*—3.25 cm.
- *Hypanthium.*—Present.
- *Flower color* (*range*).—68A to 68D.
- *Flowers persistent or self-cleaning.*—Self-cleaning.
- *Aspect.*—Facing outward and upward.
- *Bud dimensions.*—6 mm in length and 1 mm in width.
- *Bud shape.*—Linear.
- *Bud color* (*range*).—58A to 58B.
- *Bud surface.*—Pubescent.
- *Bud apex.*—Acute.
- *Petals.*—Four in number.
- *Petal shape.*—Obovate.

*Abaxial petal color* (*range*).—68A to 68D.
*Adaxial petal color* (*range*).—68A to 68D.
*Vein color.*—67B.
*Petal length.*—15 mm.
*Petal width.*—9 mm.
*Petals fused or unfused.*—Unfused.
*Petal margin.*—Entire.
*Petal apex.*—Broad acute.
*Petal base.*—Attenuate.
*Petal surfaces* (*abaxial and adaxial*).—Glabrous.
*Calyx.*—Petaloid.
*Sepals.*—4 in number.
*Sepal margin.*—Entire.
*Sepal apex.*—Acute.
*Sepals fused or unfused.*—Unfused.
*Sepal color* (*abaxial and adaxial surface*).—71B.
*Sepal shape.*—Linear.
*Sepal dimensions.*—6 mm in length and 1.50 mm in width.
*Sepal surface* (*abaxial and adaxial*).—Glabrous.
*Peduncle length* (*average*).—2 cm.
*Peduncle diameter* (*average*).—2.50 mm.
*Peduncle shape.*—Cylindrical.
*Peduncle color* (*range*).—59A to 59C.
*Peduncle surface.*—Glabrous.
*Flower fragrance.*—None observed.

Reproductive organs:
*Stamens.*—8 in number.
*Stamen color* (*range*).—68B to 68D.
*Stamen length* (*average*).—9 mm.
*Anther length.*—3 mm.
*Anther color.*—67A.
*Pollen color.*—158A.
*Pollen quantity* (*range*).—Large to moderate amount.
*Pistil.*—One in number.
*Pistil length.*—14 mm.
*Pistil color.*—68C.
*Pistil shape.*—Filament.
*Stigma shape.*—4-lobed.
*Stigma color.*—68D.
*Stigma dimensions.*—1.5 mm in height and 3 mm in width.
*Ovary position.*—Inferior.
*Ovary color.*—144A.
*Ovary shape.*—Ovoid.
*Ovary dimensions.*—1 mm in height and 1.5 mm in width.

Seed production: No seed observed to date.

The invention claimed is:

1. A new and distinct cultivar of *Gaura* plant named 'PASSIONATE RAINBOW PETITE' as described and illustrated herein.

* * * * *